US00PP20402P2

(12) United States Plant Patent

Van Zanten

(10) Patent No.: US PP20,402 P2

(45) Date of Patent: Oct. 6, 2009

(54) *CHRYSANTHEMUM* PLANT NAMED 'GG GOLDN 08'

(50) Latin Name: *Chrysanthemum morifolium*
Varietal Denomination: GG GOLDN 08

(75) Inventor: Leo Van Zanten, Oxnard, CA (US)

(73) Assignee: GroLink Plant Company, Oxnard, CA (US)

( * ) Notice: Subject to any disclaimer, the term of this patent is extended or adjusted under 35 U.S.C. 154(b) by 0 days.

(21) Appl. No.: 12/218,868

(22) Filed: Jul. 18, 2008

(51) Int. Cl.
*A01H 5/00* (2006.01)

(52) U.S. Cl. ..... Plt./296

(58) Field of Classification Search ..... Plt./296, Plt./295

See application file for complete search history.

*Primary Examiner*—June Hwu

(74) *Attorney, Agent, or Firm*—Mark P. Bourgeois

(57) ABSTRACT

A new and distinct *Chrysanthemum* plant cultivar is disclosed, characterized by large daisy type inflorescences, consistent flowering response to short days, blooming consistently after 49 days of short day length, bronze orange ray florets, and a free branching habit.

1 Drawing Sheet

Latin name of the genus and species: *Chrysanthemum morifolium.*

Variety denomination: 'GG GOLDN 08'.

BACKGROUND OF THE INVENTION

The new cultivar 'GG GOLDN 08' is a product of a cross between the male parent 'Brenner' (not patented in the United States) and the female parent 'OS1101' (unpatented). The new cultivar was discovered and selected by Leo Van Zanten in August of 2003 in Oxnard, Calif.

Asexual reproduction of the new cultivar 'GG GOLDN 08' by terminal cuttings was performed in Oxnard, Calif., and has shown that the unique features of this new cultivar are stable and reproduced true to type on successive generations.

SUMMARY OF THE INVENTION

The cultivar 'GG GOLDN 08' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'GG GOLDN 08.' These characteristics in combination distinguish 'GG GOLDN 08' as a new and distinct *Chrysanthemum* cultivar:

1. Large bronze, daisy-type inflorescences;
2. Free branching habit; and
3. Consistent flowering response to short days, blooming consistently after 48 days of short day length.

Plants of the new cultivar 'GG GOLDN 08' are similar to plants of the male parent variety, 'Brenner' in most horticultural characteristics, however plants of the new cultivar 'GG GOLDN 08' are shorter. Also, the new cultivar 'GG GOLDN 08' has a smaller inflorescence diameter and longer inflorescence longevity. Additionally, the ray florets of 'GG GOLDN 08' are bronze compared to the yellow ray florets of the male parent. Finally, 'GG GOLDN 08' has a shorter response time.

Plants of the new cultivar 'GG GOLDN 08' are similar to plants of the female parent variety, 'OS1101' in most horticultural characteristics, however plants of the new cultivar 'GG GOLDN 08' are shorter but have a wider plant spread. Also, the new cultivar 'GG GOLDN 08' has a daisy inflorescence form compared to the anemone-type form of the female parent. Additionally, the ray florets of 'GG GOLDN 08' are a darker bronze than the female parent. Finally, 'GG GOLDN 08' has a shorter response time.

In comparison to the commercially available variety 'GG GTCHA 05' (U.S. Plant Pat. No. 18,329), 'GG GOLDN 08' is taller and wider. Additionally, the new variety 'GG GOLDN 08' has a larger inflorescence diameter and darker bronze-orange ray florets. Finally, the new variety 'GG GOLDN 08' has more whorls per inflorescence and a pure yellow-orange disc compared to the orange and green disc of the comparable variety.

BRIEF DESCRIPTION OF THE PHOTOGRAPH

The accompanying photograph illustrates in full color a typical plant of 'GG GOLDN 08' grown in a 6 inch container. One cutting was used in the pot, planted mid May and grown under outdoor field conditions. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'GG GOLDN 08' plants grown in Oxnard, Ventura County, Calif., during the months of May through October 2006. The growing temperature ranged from 12° C. to 15° C. at night to 12° C. to 20° C. during the day. Measurements and numerical values represent averages of typical flowering types.

Botanical classification: *Chrysanthemum morifolium 'GG GOLDN* 08.'

Commercial classification: Pot-type *Chrysanthemum.*

PROPAGATION

Time to rooting: 7 to 14 days at approximately 21° C.
Root description: Fine, fibrous.

PLANT

Growth habit: Mounding herbaceous perennial.
Height: Approximately 35 cm.
Plant spread: Approximately 48 cm.
Growth rate: Moderate.
Branching characteristics: Free Branching.
Length of lateral branches: Approximately 31 cm.
Number of leaves per lateral branch: Approximately 35.
Age of plant described: Approximately 106 days.

FOLIAGE

Leaf:
*Arrangement.*—Alternate single.
*Average length.*—Approximately 6.8 cm.
*Average width.*—Approximately 3.8 cm.

*Shape of blade.*—Ovate.
*Apex.*—Acuminate.
*Base.*—Attenuate.
*Attachment.*—Stalked.
*Margin.*—Palmately lobed, sinuses between lateral lobes parallel to divergent.
*Texture of top surface.*—Lightly pubescent.
*Texture of bottom surface.*—Lightly pubescent.
*Leaf internode length.*—Approximately 1.6 cm.
*Color.*—Young foliage upper side: Near Green 138C. Young foliage under side: Near Green 137B. Mature foliage upper side: Near Green 137A. Mature foliage under side: Near Green 137C.
*Venation.*—Type: Palmately net. Venation color upper side: Near Green 138C. Venation color under side: Near Green 138C.
Petiole:
*Average length.*—Approximately 1.9 cm.
Color.—Near Green 138C.
Diameter.—Approximately 0.3 cm.

BLOOM

Inflorescence:
*Flowering habit.*—Induced by darkness period greater than 13.5 hours, approximately 49 days of appropriate day length required to induce and develop blooms.
*Inflorescence form.*—Daisy.
*Number of inflorescences per lateral branch.*—Approximately 25.
*Inflorescence diameter.*—Approximately 9 cm.
*Inflorescence depth.*—Approximately 3 cm.
*Inflorescence disc diameter.*—Approximately 1.3 cm.
*Inflorescence longevity on plant.*—Approximately 33 to 40 days.
*Persistence.*—Persistent.
*Fragrance.*—None detected.
Ray florets:
*Appearance.*—Matte.
*Texture.*—Smooth.
*Average number of ray florets per inflorescence.*—31.
*Average number of whorls.*—3.
*Shape.*—Oblanceolate reflexed.
*Aspect.*—Semi-upright.
*Margin.*—Entire.
*Apex.*—Obtuse.
*Base.*—Fused along 10% of its length.
*Length.*—Approximately 4.2 cm.
*Width.*—Approximately 1 cm.
*Color.*—Upper surface at first opening: Near Yellow 7A. Upper surface at maturity: Near Yellow-Orange 14A at base and near Greyed-Orange 167B at tip. Upper surface at fading: Near Yellow-Orange 20A. Under surface at first opening: Near Greyed-Orange 167B. Under surface at maturity: Near Yellow 10A with the very tip of the floret Near Greyed-Orange 167B. Under surface at fading: Near Yellow-Orange 20A with the very tip showing Shades of Greyed-Orange 167C.
Disc florets:
*Appearance.*—Shiny.
*Texture.*—Smooth.
*Average number of florets per disc.*—Approximately 229.
*Shape.*—Cylindric.
*Apex.*—Obtuse.
*Average length.*—Approximately 0.6 cm.
*Average width.*—Approximately 0.1 cm.
*Color.*—At first opening: Near Yellow 12A. At maturity: Near Yellow 12A. At fading: Near Yellow 12B.
Peduncle:
*Length.*—At terminal end (shortest): Approximately 3.8 cm. At lateral end (longest): Approximately 9.5 cm.
*Angle to stem.*—Acute.
*Strength.*—Moderate.
*Color.*—Near Green 137C.
*Habit.*—Upright.
*Diameter.*—Approximately 0.2 cm.
*Surface texture.*—Lightly pubescent.
Inflorescence bud:
*Length.*—Approximately 0.6 cm.
*Diameter.*—Approximately 0.8 cm.
*Form.*—Globular.
*Color.*—Near Greyed-Orange 167A.
Involucral bracts (phyllaries):
*Appearance.*—Matte.
*Texture.*—Lightly pubescent.
*Number.*—Approximately 24.
*Shape.*—Lanceolate.
*Margin.*—Entire.
*Apex.*—Obtuse.
*Length.*—Approximately 0.9 cm.
*Width.*—Approximately 0.3 cm.
*Color.*—Upper side: Near Green 137A. Under side: Near Green 137C.

REPRODUCTIVE ORGANS

Ray florets:
*Number of pistils per floret.*—1.
*Stigma shape.*—2 branched.
*Stigma color.*—Near Yellow 9A.
*Style color.*—Near Yellow-Green 154A.
*Style length.*—Approximately 0.3 cm.
*Stamens.*—Absent.
Disc florets:
*Number of pistils per floret.*—1.
*Stigma shape.*—Cylindric.

*Stigma color.*—Near Yellow 9A.
*Style length.*—Approximately 0.2 cm.
*Style color.*—Near Yellow-Green 154B.
*Number of stamens per floret.*—Approximately 5.
*Anther shape.*—Tubular.
*Anther color.*—Near Yellow 9A.
*Pollen color.*—No pollen detected.

OTHER CHARACTERISTICS

Disease resistance: Neither resistance nor susceptibility to diseases or pests has been observed in this variety.

Drought tolerance/cold tolerance: Flowering plants are hardy to low temperatures about −2° C. Non-flowering plants are hardy in the approximate range of 3° C. to −6° C., depending upon duration of cold and amount of moisture in the soil. With adequate water plants are hardy to a high temperature of 45° C.

Fruit/seed production: Commercially, this plant is not used or observed in a stage where seeds would be produced. Therefore, seed production has not been observed.

What is claimed is:

1. A new and distinct cultivar of *Chrysanthemum* plant named 'GG GOLDN 08' as herein illustrated and described.

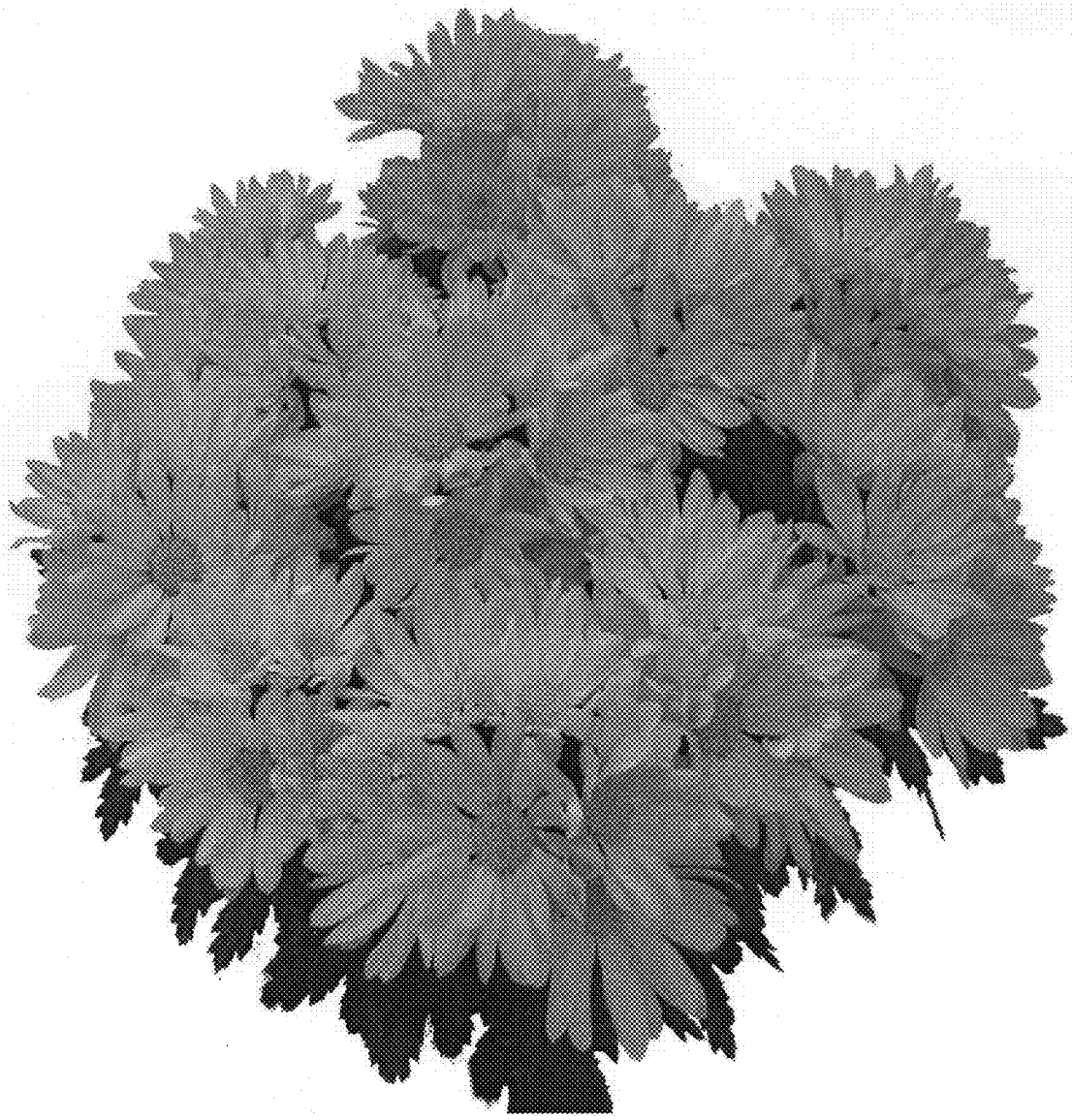

* * * * *